(12) United States Patent
Goldstein et al.

(10) Patent No.: US 12,225,913 B2
(45) Date of Patent: *Feb. 18, 2025

(54) CANNABIS COMPOSITIONS AND METHODS OF MAKING THE SAME

(71) Applicant: 5071, Inc., Commerce City, CO (US)

(72) Inventors: Jeremy H. Goldstein, Brooklyn, NY (US); Justin E. Singer, Boulder, CO (US); Adrian Verwolf, Denver, CO (US); Garret Nicodemus, Denver, CO (US)

(73) Assignee: 5071, Inc., Commerce City, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/340,572

(22) Filed: Jun. 23, 2023

(65) Prior Publication Data

US 2023/0413845 A1 Dec. 28, 2023

Related U.S. Application Data

(63) Continuation of application No. 16/571,610, filed on Sep. 16, 2019, now Pat. No. 11,980,204, which is a continuation of application No. 15/084,954, filed on Mar. 30, 2016, now abandoned.

(60) Provisional application No. 62/163,316, filed on May 18, 2015.

(51) Int. Cl.

| | |
|---|---|
| *A23L 2/395* | (2006.01) |
| *A23F 3/14* | (2006.01) |
| *A23L 2/52* | (2006.01) |
| *A23L 33/105* | (2016.01) |
| *A23L 33/115* | (2016.01) |
| *A23P 10/40* | (2016.01) |
| *A61K 9/00* | (2006.01) |
| *A61K 9/16* | (2006.01) |
| *A61K 31/05* | (2006.01) |
| *A61K 31/352* | (2006.01) |

(52) U.S. Cl.
CPC .............. *A23F 3/14* (2013.01); *A23L 2/52* (2013.01); *A23L 33/105* (2016.08); *A23L 33/115* (2016.08); *A23P 10/40* (2016.08); *A61K 9/0095* (2013.01); *A61K 9/1617* (2013.01); *A61K 9/1623* (2013.01); *A61K 9/1658* (2013.01); *A61K 9/1664* (2013.01); *A61K 31/05* (2013.01); *A61K 31/352* (2013.01); *A23V 2002/00* (2013.01)

(58) Field of Classification Search
CPC ......... A23V 2250/21; A23L 2/60; A23L 2/00; A23L 2/39; A23L 2/395; A23L 33/105; A23L 33/115; A23L 2/52; A23P 10/30; A23P 10/40; A61K 9/0095; A23F 3/14
See application file for complete search history.

(56) References Cited

U.S. PATENT DOCUMENTS

| | | |
|---|---|---|
| 3,506,457 A | 4/1970 | Gidlow et al. |
| 4,830,862 A | 5/1989 | Braun et al. |
| 5,118,511 A | 6/1992 | Horn et al. |
| 5,284,674 A | 2/1994 | Fazio |
| 5,554,400 A | 9/1996 | Stipp |
| 6,287,592 B1 | 9/2001 | Dickinson |
| 6,365,176 B1 | 4/2002 | Bell |
| 6,440,449 B1 * | 8/2002 | Hirschberg ............ A23B 4/033 426/456 |
| 6,482,433 B1 | 11/2002 | DeRoos |
| 6,858,245 B2 | 2/2005 | DeConinck |
| 6,887,493 B2 | 5/2005 | Shefer et al. |
| 7,147,882 B2 | 12/2006 | Girsh |
| 8,734,885 B2 | 5/2014 | Sweeney |
| 8,808,734 B2 | 8/2014 | Winnicki |
| 8,980,941 B2 | 3/2015 | Hospodor |
| 9,474,725 B1 | 10/2016 | Reillo et al. |
| 9,629,886 B2 | 4/2017 | Franklin et al. |
| 9,839,612 B2 | 12/2017 | Reillo |
| 9,937,147 B2 | 4/2018 | DeGeeter |
| 9,972,680 B2 | 5/2018 | Reillo |
| 9,974,739 B2 | 5/2018 | Reillo |
| 10,016,363 B2 | 7/2018 | Bromley |
| 10,028,919 B2 | 7/2018 | Kaufman |
| 10,084,044 B2 | 9/2018 | Reillo |
| 10,103,225 B2 | 10/2018 | Reillo |
| 10,374,036 B2 | 1/2019 | Reillo |
| 10,381,440 B2 | 8/2019 | Reillo |
| 10,413,845 B1 | 9/2019 | Tegen et al. |
| 10,414,709 B1 | 9/2019 | Tegen et al. |
| 10,756,180 B2 | 8/2020 | Reillo |
| 2002/0127303 A1 | 9/2002 | Chen et al. |
| 2002/0136752 A1 | 9/2002 | Whittle et al. |
| 2002/0188024 A1 | 12/2002 | Chilton et al. |
| 2004/0234579 A1 | 11/2004 | Finke |
| 2005/0077497 A1 | 4/2005 | Anderson |
| 2007/0104741 A1 | 5/2007 | Murty et al. |

(Continued)

FOREIGN PATENT DOCUMENTS

| | | |
|---|---|---|
| CA | 2952335 A1 | 6/2017 |
| CN | 101904401 A | 12/2010 |

(Continued)

OTHER PUBLICATIONS

Datbase WPI, Week 201381 Thomas Scientific. XP002787597, May 22, 2013, London, GB; AN 2013-R00947 & CN 103110582A (3 pages).

(Continued)

*Primary Examiner* — Hong T Yoo

(74) *Attorney, Agent, or Firm* — FisherBroyles, LLP; Andrew K. Gonsalves; Craig W. Mueller

(57) ABSTRACT

Disclosed herein are new cannabis compositions. In one embodiment, these new cannabis compositions are beverages, such as tea. In one embodiment, these new cannabis compositions are dehydrated beverages, such as powders or crystalline forms, which can be mixed with other components, like tea, and added to water.

21 Claims, No Drawings

(56) References Cited

U.S. PATENT DOCUMENTS

| | | |
|---|---|---|
| 2007/0213298 A1 | 9/2007 | Rongved et al. |
| 2008/0008781 A1 | 1/2008 | Sweeney et al. |
| 2008/0064679 A1 | 3/2008 | Martin et al. |
| 2008/0206325 A1 | 8/2008 | Bouquerand et al. |
| 2008/0254153 A1 | 10/2008 | Wang et al. |
| 2009/0095164 A1 | 4/2009 | Celeste |
| 2009/0162524 A1 | 6/2009 | Rivera et al. |
| 2009/0264475 A1 | 10/2009 | Schwartz |
| 2010/0034888 A1 | 2/2010 | Pellikaan et al. |
| 2011/0092583 A1 | 4/2011 | Murty et al. |
| 2012/0043242 A1 | 2/2012 | Hospodor |
| 2012/0095087 A1 | 4/2012 | Hyatt |
| 2012/0231083 A1 | 9/2012 | Carley et al. |
| 2013/0078356 A1 | 3/2013 | Mackereth et al. |
| 2013/0089600 A1 | 4/2013 | Winnicki |
| 2013/0164412 A1 | 6/2013 | Amrani |
| 2013/0196022 A1 | 8/2013 | Holma |
| 2013/0296415 A1 | 11/2013 | Goskonda et al. |
| 2013/0309291 A1 | 11/2013 | Stoll |
| 2013/0337113 A1 | 12/2013 | Clark et al. |
| 2014/0100269 A1 | 4/2014 | Goskonda et al. |
| 2014/0295049 A1 | 10/2014 | Ragot et al. |
| 2014/0328997 A1 | 11/2014 | Raskin et al. |
| 2014/0357708 A1 | 12/2014 | Murty et al. |
| 2014/0370181 A1 | 12/2014 | Young et al. |
| 2015/0045282 A1 | 2/2015 | Elsohly et al. |
| 2015/0057341 A1 | 2/2015 | Perry |
| 2015/0079235 A1 | 3/2015 | Wright et al. |
| 2015/0110924 A1 | 4/2015 | Bromley |
| 2015/0258040 A1 | 9/2015 | Lynch et al. |
| 2015/0352044 A1 | 12/2015 | Benson et al. |
| 2016/0051510 A1 | 2/2016 | Allen et al. |
| 2016/0058866 A1 | 3/2016 | Sekura et al. |
| 2016/0143972 A1 | 5/2016 | Stebbins et al. |
| 2016/0324776 A1 | 11/2016 | Glatzel |
| 2017/0049830 A1 | 2/2017 | Raderman |
| 2017/0172977 A1 | 6/2017 | Kleidon et al. |
| 2018/0007924 A9 | 1/2018 | Goldstein et al. |
| 2018/0125980 A1 | 5/2018 | Finley et al. |
| 2018/0360704 A1 | 12/2018 | Riefler et al. |
| 2019/0015383 A1 | 1/2019 | Woelfel et al. |
| 2019/0240148 A1 | 8/2019 | Riefler et al. |
| 2019/0276420 A1 | 9/2019 | Tegen et al. |
| 2020/0008441 A1 | 1/2020 | Goldstein et al. |
| 2020/0071285 A1 | 3/2020 | Tegen et al. |
| 2020/0113825 A1 | 4/2020 | Victor et al. |

FOREIGN PATENT DOCUMENTS

| | | |
|---|---|---|
| CN | 104619318 A | 5/2015 |
| EP | 1437136 A1 | 7/2004 |
| WO | 1999035917 A1 | 7/1999 |
| WO | 2012130278 A1 | 10/2012 |
| WO | 2013138906 A1 | 9/2013 |
| WO | 2014186896 A1 | 11/2014 |
| WO | 2015024055 A1 | 2/2015 |
| WO | 2015191728 A1 | 12/2015 |
| WO | 2016186735 A1 | 11/2016 |
| WO | WO 2017/072762 A1 | 5/2017 |
| WO | 2017180954 A1 | 10/2017 |
| WO | 2017202424 A1 | 11/2017 |
| WO | 2018011808 A1 | 1/2018 |
| WO | 2018204326 A1 | 11/2018 |

OTHER PUBLICATIONS

International Search Report for PCT/US2016/025044 dated Jun. 27, 2016 (2 pages).

Grembecka, Malgorzata, "Sugar alcohols—Their Role in the Modern World of Sweeteners: a Review," Eur. Food Res. Technol., 214:1-14 (2015).

United Nations, Office on Drugs and Crime, World Drug Report 2009 Series, Why does cannabis potency matter?, Jun. 29, 2009, https://www.unodc.org/unodc/en/frontpage/2009/June/why-does-cannabis-potency-matter.html, retrieved online Dec. 7, 2021 (2009).

* cited by examiner

CANNABIS COMPOSITIONS AND METHODS OF MAKING THE SAME

CROSS-REFERENCE TO RELATED APPLICATIONS

This application is a continuation of U.S. patent application Ser. No. 16/571,610, filed on Sep. 16, 2019, which issued as U.S. Pat. No. 11,980,204 on May 14, 2024, which is a continuation of U.S. patent application Ser. No. 15/084,954, filed on Mar. 30, 2016, now abandoned, which claims the benefit of priority to U.S. Provisional Application No. 62/163,316, filed on May 18, 2015, each of which is incorporated herein by reference in its entirety.

TECHNICAL FIELD

This disclosure relates to the cannabis industry. In particular, the disclosure relates to cannabis compositions for use in the making beverages, methods of making beverages, and beverages.

BACKGROUND

Cannabis has a long history of being consumed for many purposes and in many forms. The psychoactive effects of cannabis are well known, however the medical benefits are just as useful. Treating glaucoma, pain management, appetite stimulation and easing anxiety are just a few of the potential benefits. The source of these effects are in the cannabinoids, a class of compounds found exclusively in the cannabis plant. Currently there are 483 identified compounds found in cannabis. The most well known, and in some ways the most important, is tetrahydrocannabniol (THC). THC is responsible for many of the psychoactive effects as well as the medicinal effects. Cannabidiol (CBD) is also another major cannabinoid comprising up to 40% of cannabis extract and could have as many health benefits as THC.

Many methods exist for extracting the cannabinoids from the cannabis plant. A common method is alcohol extraction. Using a solvent to extract the cannabinoids and then evaporating the alcohol leaving a resin. Further extraction and evaporation can yield a product that is closer to a solid. Another common method for the purposes of making edibles is placing the cannabis leaves in butter, heavy cream, oil, etc. and then heating to extract the cannabinoids. The end product is then used as an ingredient in baking or cooking which usually results in a high caloric food due to the fat needed to extract the cannabinoids. Cannabinoids are soluble in fats and alcohols. Which is why when making cannabis tea the cannabinoids have to be already extracted. Just placing cannabis leaves in hot water will not effectively extract any of the vital cannabinoids.

However, the state of the art has many shortcomings. The cannabis arts do not have homogenous cannabis beverages. Existing cannabis beverages include large amounts of caloric material. Existing cannabis beverages are not capable of providing consistent cannabinoid concentrations, especially at low cannabinoid concentrations.

There exists a need for homogenous cannabis beverages. In particular there exists a need for beverages providing a consistent amount of the cannabinoid, especially at low doses.

DETAILED DESCRIPTION

Disclosed herein are new cannabis compositions. In one embodiment, these new cannabis compositions are beverages, such as tea. In one embodiment, these new cannabis compositions are dehydrated beverages, such as powders or crystalline forms, which can be mixed with other components, like tea, and added to water.

In one embodiment, the disclosed cannabis compositions are homogenous. In one embodiment, the disclosed cannabis compositions include a surfactant and a carrier oil. In one embodiment, the disclosed cannabis compositions are consistent with respect to cannabinoid amount. In one embodiment, the disclosed cannabis compositions are low-calorie cannabis beverages, such as low calorie cannabis teas.

Disclosed herein are new compositions comprising:
a cannabinoid,
a surfactant, and
a carrier oil.

As used herein the term "cannabinoid" refers to a compound that acts on the cannabinoid receptor. In one embodiment of this disclosure, the compositions are low dose compositions having 0.1 to 10 mg of cannabinoid. In some embodiments, the composition comprises between 0.5 to 5 mg.

In other embodiments of this disclosure, higher amounts of cannabinoid can be used, such as more than 10 mg, for example 20-500 mg or 50-200 mg.

Examples of cannabinoids are tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid, delta-9-tetrahydrocannabivarin, delta-9-tetrahydrocannabiorcolic acid, delta-9-tetrahydrocannabiorcol, delta-7-cis-iso-tetrahydrocannabivarin, delta-8-tetrahydrocannabinolic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxy-cannabitriolvarin, dehydrocannabifuran, cannabifuran, cannabichromanon, cannabicitran, 10-oxo-delta-6a-tetrahydrocannabinol, delta-9-cis-tetrahydrocannabinol, 3, 4, 5, 6-tetrahydro-7-hydroxy-alpha-alpha-2-trimethyl-9-n-propyl-2, 6-methano-2H-1-benzoxocin-5-methanol-cannabiripsol, trihydroxy-delta-9-tetrahydrocannabinol, and cannabinol. Examples of cannabinoids within the context of this disclosure include tetrahydrocannabinol and cannabidiol.

As used herein, the term "tetrahydrocannabinol" (THC) refers to a compound having the following structural formula:

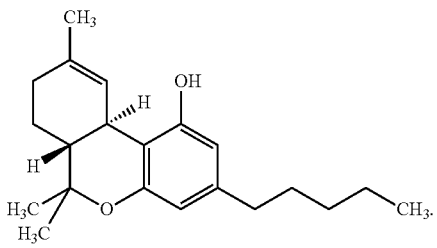 [SMILES: CCCCCc1cc(O)c2c(c1)OC(C)(C)[C@@H]1CCC(C)=C[C@@H]21]

As used herein, the term "cannabidiol" (CBD) refers to a compound having the following structural formula:

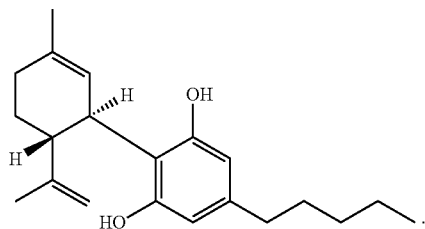 [SMILES: C=C(C)[C@@H]1CCC(C)=C[C@H]1c1c(O)cc(CCCCC)cc1O]

As used herein the term "surfactant" refers to a compound that lowers the surface tension between two liquids or between a liquid and solid. Surfactants can be anionic, cationic, non-ionic and amphoteric. Examples of surfactants are ammonium lauryl sulfate, dioctyl sodium sulfosuccinate, perflurooctanoic acid, potassium lauryl sulfate, soap, sodium dodecyl sulfate, sodium dodecylbenzenesulfonate, sodium laureth sulfate, sodium lauroyl sarcosinate, sodium myreth sulfate, sodium pareth sulfate, sodium stearate, perflurobutanesulfonic acid, perfluorononanoic acid, perlurooactanesulfonic acid, benzalkonium chloride, benzethonium chloride, bronidox, dimethyldioctadecylammonium chloride, lauryl methyl gluceth-10 hydroxypropyl dimonium chloride, cetrimonium bromide, cetrimonium chloride, tetramethylammonium hydroxide, cetomacrogol 1000, cetostearyl alcohol, cetyl alcohol, cocamide DEA, cocamide MEA, NP-40, octaethylene glycol monododecyl ether, N-octyl beta-D-thoglucopyranoside, octyl glucoside, oleyl alcohol, decyl glucoside, pentaethylene glycol monododecyl ether, poloxamer 407, polyglycerol polyricinolate, polysorbate, polysorabte 20, IGEPAL CA-630, isoceteth-20, lauryl glucoside, lecithin, sodium lauroampoacetate, cocamidopropyl betaine, hydroxysultaine, stearyl alcohol, decyl glucoside, octaethylene glycol monododecyl ether, nonoxynol-9, monolaurin, oleyl alcohol, poloxamer, sorbitan monostearate, polysorbate 80 and glycerol monostearate. Examples of surfactants within the context of this disclosure include polysorbate 80 and/or glycerol monostearate.

As used herein, the term "polysorbate 80" refers to a compound having the following structure:

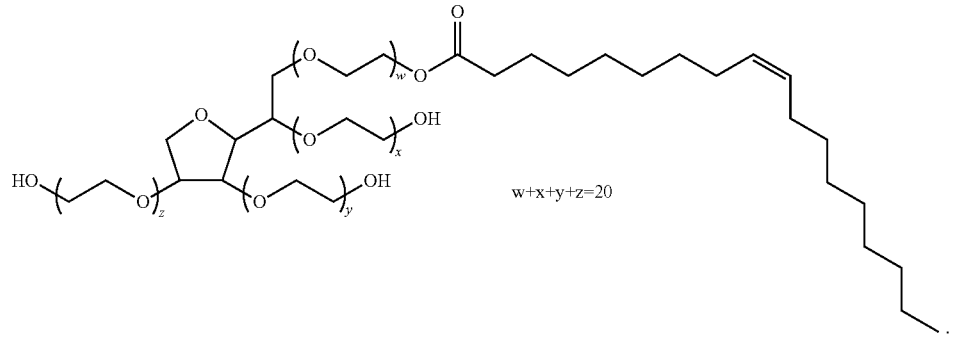

As used herein the term "glycerol monostearate" refers to a compound having the following structure:

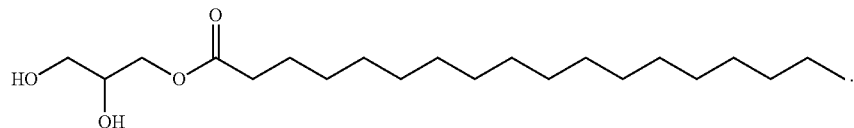 [SMILES: CCCCCCCCCCCCCCCCCC(=O)OCC(O)CO]

As used herein the term "carrier oil" refers to an oil that can be used to form a homogenized mixture with cannabis oil. Examples include coconut oil, palm oil, palm kernel oil, hemp oil, caproic acid and caprylic acid. One example of carrier oils within the context of this disclosure is medium chain triglycerides. Another example of a carrier oil within the context of this disclosure is coconut oil. Another example of a carrier oil within the context of this disclosure is hemp oil.

As used herein the term coconut oil means oil extracted from the kernel or meat of coconuts. Coconut is the fruit of the coconut palm. Coconut oil is noted for it's high saturated content. Examples include lauric acid, myristic acid, palmitic acid, and decanoic acid.

As used herein the term hemp oil refers to oil obtained from hemp seeds. Hemp seeds come from a variety of the *Cannabis sativa* plant that does not contain a high amount of tetrahydrocannabinol. The oil is about 80% essential fatty acids. Examples include linolenic acid, omega-6, alpha-linolenic acid, and omega-3.

In one embodiment, the composition comprises a cannabinoid, a surfactant, a carrier oil, and a sugar alcohol.

As used herein the term "sugar alcohol" refers to alcohols prepared from sugars with the general chemical formula $HOCH_2(CHOH)_nCH_2OH$. Examples include glycerol, erythritol, threitol, arabitol, xylitol, mannitol, ribitol, mannitol, galacitol, fucitol, inositol, volemitol, maltitol, lacitol, malootetraitol, polyglycitol, sorbitol, iditol, isomalt, and maltotriitol. Examples of sugar alcohols within the context of this disclosure include glycerol/glycerin or sorbitol.

As used herein, the term "glycerol" refers to a compound having the following structure:

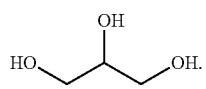

As used herein, the term "sorbitol" refers to a compound having the following structure:

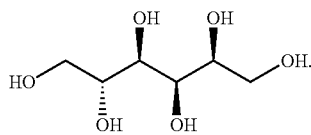

In one embodiment, the composition disclosed herein comprises a cannabinoid, a surfactant, a carrier oil, and a gelling agent.

As used herein, the term "gelling agent" means a substance that dissolves in the liquid phase and forms a weak cohesive internal structure. Examples include natural gums, starches, pectins, agar-agar, and gelatin.

As used herein, the term "gelatin" refers to a gelling agent derived from the collagen of various all byproducts.

In one embodiment, the composition comprises a cannabinoid, a surfactant, a carrier oil, and has less than 10 mass % water. In one embodiment, the composition is a solid. In one embodiment, the composition is a granual.

As used herein, the term "less than 10 mass % water" means less than 10% of water, by mass, of the composition.

In one embodiment, the composition comprises a cannabinoid, a surfactant, a carrier oil, and has more than 95 mass % water.

As used herein, the term "more than 95 mass % water" means less than 95% of water, by mass, of the composition.

In one embodiment, the composition comprises a cannabinoid, a surfactant, a carrier oil, and a flavoring agent.

As used herein, the term "flavoring agent" means a compound that adds a flavor to a composition. A few examples of flavoring agents include amyl acetate, benzaldehyde, ethyl butyrate, methyl anthranilate, methyl salicylate, fumaric acid, diacetyl, cinnamaldehyde, ethyl propionate, limonene, ethyl decadienoate, allyl hexanoate, ethyl maltol, ethylvanillin, and methyl salicylate.

In one embodiment, the composition comprises a coloring agent. As used herein, the term "coloring agent" means any substance that adds or changes the color of the substance to which the coloring agent is added. Within the context of this application, examples of the term coloring agent include any dye, pigment or substance that imparts color when it is added to food or drink. The coloring agent can be natural or non-natural. Such agents come in many forms, including liquids, powders, gels, dyes, lakes, and pastes. In one exemplary embodiment, one or more coloring agents can be added to the compositions of this disclosure to match the coloring between two ingredients. In one example, brownish color is added to a compositions comprising a cannabinoid, a surfactant, and a carrier oil in order to make the said compositions take on the color of natural tea.

In one embodiment, the composition comprises a cannabinoid, a surfactant, a carrier oil, and tea. In one embodiment the tea are tea leaves. As used herein, the term "tea" is meant to include any composition that is similar or labeled as tea, either natural or synthetic. Tea refers to both artificially flavored and/or artificially colored compositions in addition to all forms of natural tea leaves. In one embodiment, the cannabis compositions are brown granules.

As used herein the term "tea leaves" refers to forms of the plant *Camellia sinensis*.

In one embodiment, the composition comprises less than 4 grams of caloric mass. In one embodiment the caloric mass is less than 2 grams. As the herein the term "caloric mass" means mass metabolized by humans to generate energy. Examples include carbohydrates and proteins which give 4 cal/gram and fats which give 9 cal/gram.

In one embodiment, the composition comprises 0.5 to 5 mg of the cannabinoid is present in a consistent amount, having less than 0.2 mg of deviation across sample portions of the composition.

As used herein the term "consistent amount" means a collection of samples would all have relatively similar amounts of the cannabinoid. Similar means limited amount of deviation in the mass of the cannabinoid. For example, if a collection of compositions were analyzed to determine the mass of cannabinoid present, each sample in that collection would have a similar mass of cannabinoid present in relation to the total amount of each composition.

In one embodiment, the composition comprises:
  cannabis oil having 1.5 to 3.5 mg of THC;
  glycerine,
  sorbitol,
  gelatin,
  glycerol monostearate,
  polysorbate 80, and
  coconut oil.

In one embodiment, the composition comprises:
  cannabis oil having 1.5 to 3.5 mg of THC;
  glycerine,
  sorbitol,
  gelatin,
  glycerol monostearate,
  polysorbate 80,
  coconut oil, and
  tea.

In one embodiment, the composition comprises:
  cannabis oil having 1.5 to 3.5 mg of THC;
  glycerine,
  sorbitol,
  gelatin, glycerol monostearate,
polysorbate 80,
coconut oil,
and greater than 95 mass % of water.

In one embodiment, the composition comprises:
cannabis oil having 1.5 to 3.5 mg of THC;
glycerine,
sorbitol,
gelatin,
glycerol monostearate,
polysorbate 80,
coconut oil,
and less than 5 mass % of water.

EXAMPLES

Although the present invention herein has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. As used herein, the term "include" or "comprising" and its grammatical variants are intended to be non-limiting, such that recitation of an item or items is not to the exclusion of other like items that can be substituted or added to the recited item(s).

The gram amounts of ingredients depend on the batch size. Gram amounts for batches can be determined by following the mixing guidelines below.

| Ingredient | Parts |
|---|---|
| Water | 8-12 |
| Surfactant | 1-1.5 |
| Carrier Oil | 4 |
| Cannabinoid | 1 |
| Sugar alcohol | 30-70 |
| Gelling agent | 0.3-0.5 |

Example 1

1) Surfactants were added to a beaker and heated to 80 C with a hot plate for 10 minutes to provide a homogeneous surfactant blend.
2) Carrier oil and cannabis oil were added to the surfactant blend and stirred for 10 minutes at 60 C, to provide a homogenous mixture.
3) A first sugar alcohol and gelling agent were added to water at 40 C. The mixture was heated to 80 C.
4) A second sugar alcohol was added to the mixture of sugar alcohol and gelling agent over the course of 5 minutes and mixed until well blended.
5) The sugar blend was added to the mixture of cannabis oil, carrier oil and surfactant blend over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

Example 2

1) Glycerol monostearate and polysorbate 80 were added to a beaker and heated to 80 C with a hot plate for 10 minutes to provide a homogeneous surfactant blend.
2) Carrier and cannabis oil were added to the surfactant blend and stirred for 10 minutes at 60 C, to provide a homogenous mixture.
3) Glycerin and gelatin were added to water at 40 C. The mixture was heated to 80 C.
4) Sorbitol was added to the mixture of glycerin and gelatin over the course of 5 minutes and mixed until well blended.
5) The blend of sorbitol, glycerine, and gelatin was added to the mixture of cannabis oil, coconut oil, glycerol monostearate, and polysorbate 80 over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

Example 3

1) Surfactants were added to a beaker and heated to 80 C with a hot plate for 10 minutes to provide a homogeneous surfactant blend.
2) Carrier oil and CBD oil were added to the surfactant blend and stirred for 10 minutes at 60 C, to provide a homogenous mixture.
3) A first sugar alcohol and gelling agent were added to water at 40 C. The mixture was heated to 80 C.

4) A second sugar alcohol was added to the mixture of sugar alcohol and gelling agent over the course of 5 minutes and mixed until well blended.
5) The sugar blend was added to the mixture of CBD oil, carrier oil and surfactant blend over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

Example 4

1) Surfactants were added to a beaker and heated to 80 C with a hot plate for 10 minutes to provide a homogeneous surfactant blend.
2) Coconut oil and cannabis oil were added to the surfactant blend and stirred for 10 minutes at 60 C, to provide a homogenous mixture.
3) A first sugar alcohol and gelling agent were added to water at 40 C. The mixture was heated to 80 C.
4) A second sugar alcohol was added to the mixture of sugar alcohol and gelling agent over the course of 5 minutes and mixed until well blended.
5) The sugar blend was added to the mixture of cannabis oil, coconut oil and surfactant blend over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

Example 5

1) Surfactants were added to a beaker and heated to 80 C with a hot plate for 10 minutes to provide a homogeneous surfactant blend.
2) Hemp oil and cannabis oil were added to the surfactant blend and stirred for 10 minutes at 60 C, to provide a homogenous mixture.
3) A first sugar alcohol and gelling agent were added to water at 40 C. The mixture was heated to 80 C.
4) A second sugar alcohol was added to the mixture of sugar alcohol and gelling agent over the course of 5 minutes and mixed until well blended.
5) The sugar blend was added to the mixture of cannabis oil, hemp oil and surfactant blend over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

Example 6

1) Surfactants were added to a beaker and heated to 80 C with a hot plate for 10 minutes to provide a homogeneous surfactant blend.
2) Carrier oil and cannabis oil were added to the surfactant blend and stirred for 10 minutes at 60 C, to provide a homogenous mixture.
3) A first sugar alcohol and gelatin were added to water at 40 C. The mixture was heated to 80 C.
4) A second sugar alcohol was added to the mixture of sugar alcohol and gelatin over the course of 5 minutes and mixed until well blended.
5) The sugar blend was added to the mixture of cannabis oil, carrier oil and surfactant blend over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

Example 7

To make 2300 tea sticks
1) 67 grams of glycerol monostearate and 40 grams of polysorbate 80 were added to a beaker and heated to 80 C with a hot plate for 10 minutes to provide a homogeneous surfactant blend.
2) 341 grams of coconut oil and 85 grams of THC oil were added to the surfactant blend and stirred for 10 minutes at 60 C, to provide a homogenous mixture.
3) 213 grams of glycerin and 32 grams of gelatin were added to 852 grams of water at 40 C. The mixture was heated to 80 C.

4) 4259 grams of sorbitol was added to the mixture of glycerin and gelatin over the course of 5 minutes and mixed until well blended.
5) The sugar blend was added to the mixture of THC oil, coconut oil and surfactant blend over 10 minutes and the combined mixture was heated to 80 C to provide a homogenize mixture with no phase separation.
6) The homogenized mixture was poured into trays, to create thin films, which were refrigerated for 60 minutes.
7) After cooling for 60 minutes, the films were place in a dehydrator at 40 C.
8) The films were dried for 24 hours, to provide brittle, dry films.
9) The dry films were broken into smaller pieces.
10) 10 gram portions of the broken dried films were separated by size with a sieve to remove particles less than 15 mesh size.
11) The collected particles were placed into a vacuum oven set to 40 C for 24 hrs, to provide finished dry granules.

We claim:

1. A composition comprising:
a cannabis composition comprising a collection of dry granules, wherein the collection of dry granules comprises:
(i) a solvent extracted cannabinoid or cannabinoids;
(ii) a surfactant;
(iii) a carrier oil; and
(iv) a sugar alcohol,
wherein the cannabis composition comprises a dose of 0.1 to 10 mg of the cannabinoid or cannabinoids present in a consistent amount and having less than 0.2 mg of deviation across sample portions of the composition, and
wherein the cannabis composition comprises less than 10 mass % water.

2. The composition of claim 1, wherein the cannabis composition comprises less than about 2 grams of carbohydrate and less than about 2 grams of fat.

3. The composition of claim 1, wherein the cannabis composition comprises a dose of 0.5 mg to 5 mg of the solvent extracted cannabinoid.

4. The composition of claim 1, wherein the cannabis composition comprises cannabis oil that includes the solvent extracted cannabinoid.

5. The composition of claim 1, wherein the cannabis composition is in the form of an homogenous dehydrated beverage.

6. The composition of claim 1, wherein the cannabis composition comprises less than 4 grams of caloric material.

7. The composition of claim 1, wherein the dry granules have a particle size greater than 15 mesh.

8. The composition of claim 1, wherein the solvent extracted cannabinoid or cannabinoids are selected from the group consisting of tetrahydrocannabinol (THC), cannabidiol (CBD), cannabinol (CBN), cannabitriol (CBT), cannabigerol (CBG), cannabichromene (CBC), cannabigerolic acid (CBGA), cannabidolic acid (CBDA), tetrahydrocannabivarin (THCV), cannabicyclol, cannabivarin, cannabielsoin, cannabicitran, cannabigerolic acid monomethylether, cannabigerol monomethylether, cannabigerovarinic acid, cannabigerovarin, cannabichromenic acid, cannabichromevarinic acid, cannabichromevarin, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid, delta-9-tetrahydrocannabivarin, delta-9-tetrahydrocannabiorcolic acid, delta-9-tetrahydrocannabiorcol, delta-7-cis-isotetrahydrocannabivarin, delta-8-tetrahydrocannabinolic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxycannabitriolvarin, dehydrocannabifuran, cannabifuran, cannabichromanon, cannabicitran, 10-oxo-delta-6a-tetrahydrocannabinol, delta-9-cistetrahydrocannabinol, 3, 4, 5, 6-tetrahydro-7-hydroxy-alpha-alpha-2-trimethyl-9-npropyl-2, 6-methano-2H-1-benzoxocin-5-methanol-cannabiripsol, trihydroxy-delta-9-tetrahydrocannabinol, derivatives thereof, and combinations thereof.

9. The composition of claim 1, wherein the solvent extracted cannabinoid or cannabinoids comprises at least one of cannabidiol (CBD) or tetrahydrocannabinol (THC).

10. The composition of claim 1, wherein the solvent extracted cannabinoid is cannabidiol (CBD).

11. The composition of claim 1, wherein the surfactant is an amphoteric surfactant.

12. The composition of claim 1, wherein the surfactant comprises a glucoside or lecithin.

13. The composition of claim 1, wherein the carrier oil comprises medium chain triglycerides.

14. The composition of claim 1, wherein the carrier oil comprises coconut oil.

15. The composition of claim 1, wherein the sugar alcohol is selected from the group consisting of sorbitol, maltitol, xylitol, and erythritol.

16. The composition of claim 1, wherein the sugar alcohol is sorbitol.

17. The composition of claim 1, wherein the cannabis composition further comprises a flavoring agent, a coloring agent, or both a flavoring agent and a coloring agent.

18. The composition of claim 1, wherein the cannabis composition further comprises a gelling agent comprising a natural gum or a starch or gelatin.

19. The composition of claim 18, wherein the gelling agent comprises a starch.

20. The composition of claim 18, wherein the gelling agent comprises a natural gum.

21. The composition of claim 18, wherein the gelling agent comprises gelatin.

* * * * *